(12) United States Patent
Gerlach et al.

(10) Patent No.: US 9,072,675 B2
(45) Date of Patent: Jul. 7, 2015

(54) NON-IRRITATING BENZOYL PEROXIDE

(71) Applicant: Essential Ingredients, Inc., Lawrenceville, GA (US)

(72) Inventors: Chris Gerlach, Orange Park, FL (US); Mike Davies, Dacula, GA (US); Stephen M. Dawes, Pembroke Pines, FL (US)

(73) Assignee: Essential Ingredients, Inc., Lawrenceville, GA (US)

( * ) Notice: Subject to any disclaimer, the term of this patent is extended or adjusted under 35 U.S.C. 154(b) by 0 days.

(21) Appl. No.: 14/178,460

(22) Filed: Feb. 12, 2014

(65) Prior Publication Data

US 2014/0161853 A1 Jun. 12, 2014

Related U.S. Application Data

(62) Division of application No. 13/114,076, filed on May 24, 2011, now Pat. No. 8,697,130.

(60) Provisional application No. 61/347,912, filed on May 25, 2010.

(51) Int. Cl.
| | |
|---|---|
| *A61K 8/38* | (2006.01) |
| *A61K 8/04* | (2006.01) |
| *A61K 9/14* | (2006.01) |
| *A61K 9/06* | (2006.01) |
| *A61K 9/00* | (2006.01) |
| *C07C 407/00* | (2006.01) |
| *C07C 409/34* | (2006.01) |
| *A61Q 19/00* | (2006.01) |

(52) U.S. Cl.
CPC .............. *A61K 8/38* (2013.01); *A61K 9/0014* (2013.01); *A61K 9/06* (2013.01); *A61K 9/146* (2013.01); *A61K 8/042* (2013.01); *A61Q 19/00* (2013.01); *C07C 407/003* (2013.01)

(58) Field of Classification Search
CPC ........... A61K 8/00; A61K 8/38; A61K 8/042; A61K 9/00; A61K 9/146; A61K 9/06; A61K 9/0014; C07C 407/003; A61Q 19/00
USPC ................. 568/558, 561, 566, 576; 424/489; 514/568

See application file for complete search history.

(56) References Cited

U.S. PATENT DOCUMENTS

| | | |
|---|---|---|
| 4,401,835 A | 8/1983 | Tarasov |
| 2004/0101566 A1* | 5/2004 | Cooper et al. ................ 424/489 |

* cited by examiner

*Primary Examiner* — Jane C Oswecki
(74) *Attorney, Agent, or Firm* — Banner & Witcoff, Ltd.

(57) ABSTRACT

A method of making crystalline benzoyl peroxide particles having a particle size no greater than 25 microns and formed by wet milling in the absence of solvents and wherein the crystalline benzoyl peroxide is not irritating to the skin. A method of making a therapeutic or cosmetic composition comprising a water-based gel containing the crystalline benzoyl peroxide.

19 Claims, No Drawings

NON-IRRITATING BENZOYL PEROXIDE

CROSS-REFERENCE TO RELATED APPLICATIONS

This application is a divisional of U.S. application Ser. No. 13/114,076 filed May 24, 2011, now allowed, which claims the benefit of U.S. application Ser. No. 61/347,912 filed May 25, 2010. These applications are hereby incorporated by reference in their entireties.

TECHNICAL FIELD

This disclosure relates generally to benzoyl peroxide, methods of making benzoyl peroxide particles, and compositions containing benzoyl peroxide particles.

BACKGROUND

Benzoyl peroxide ("BPO") has long been used for treatment of dermatological lesions and is also known to be an effective anti-microbial and anti-keratolytic agent useful, for example, in the treatment of acne. Benzoyl peroxide is a non-toxic, colorless, odorless, and tasteless crystalline solid with a molecular weight of 242.22 and a melting point of between about 103° and 106° C. Pure (98% active) benzoyl peroxide crystals are commercially available but are considered explosive. Hence special precautions must be taken when handling pure BPO during preparation, transportation, and storage. BPO is also commercially available as a 75% crystalline solid with 25% water and is available from a number of suppliers, primarily in the plastics industry.

Conventional BPO crystalline powder requires milling for several hours in water through high shear mills to prepare a paste having crystals that are sufficiently fine to be of acceptable texture for preparing products for topical use. Such crystals are typically average at least 20 microns. These BPO crystals may be used to treat dermatological lesions. However, the BPO crystals contacting the skin may have adverse irritative effects. The BPO Monograph finalized Mar. 4, 2010 (75 FR 9768) cites 47 FR 12430 at 12444 as disclosing that BPO "is known to be a skin irritant and sensitizer in humans." These adverse effects appear to result, at least in part, from excessive concentrations of BPO at skin areas in contact with BPO particles. Methods for avoiding such adverse effects, while still effectively utilizing BPO therapeutically, have been long-sought.

Certain prior attempts to create stable, pharmaceutically effective and dermatologically non-irritative BPO preparations have involved the production of minute BPO crystals. U.S. Pat. No. 4,401,835, issued to Tarasoy, describes a method of preparing BPO crystals that are less than ten microns in size. The method includes the steps of: (1) preparing a first solution comprising BPO and a precipitate promoting material; (2) adding the first solution to a second solution that causes the BPO to precipitate as a fine crystalline dispersion; and (3) recovering the BPO crystals which may be washed or used directly. The precipitate promoting material is a solvent for BPO that is able to produce a solution containing up to about 15% by weight BPO. In one case the solvent is dimethyl ether of 1,4:3,6-dianhydrosorbitol (dimethyl isosorbide) or tetrahydrothiophene-1,1-dioxide. The second solution is an aqueous solution of a non-toxic dispersant which is non-reactive with BPO. This dispersant is a cellulose derivative or a surfactant (non-ionic or anionic). However, solvents used to prepare the BPO crystals may have solvent residues that also irritate the skin. Hence it is desirable to provide a solvent-free, irritation-free, BPO formulation.

SUMMARY

Aspects of the present invention are directed to crystalline benzoyl peroxide particles having a particle size no greater than 25 microns and formed by wet milling in the absence of solvents; wherein the crystalline benzoyl peroxide is non-irritating to the skin.

Other aspects relate to a therapeutic or cosmetic composition comprising a water-based gel comprising crystalline benzoyl peroxide solvent-free particles having a particle size no greater than 25 microns, wherein the crystalline benzoyl peroxide is non-irritating to the skin.

Further aspects relate to a method of preparing crystalline benzoyl peroxide comprising: adding water to solid benzoyl peroxide; milling to break up agglomerates and form an aqueous benzoyl peroxide; adding a dispersion system and mixing; adjusting the pH to 2.8 to 6.6; and milling to a particle size not more than 25 microns.

DETAILED DESCRIPTION OF PREFERRED EMBODIMENTS

It was discovered that BPO can be produced in a form that is devoid of particles greater than 25 microns and essentially free of solvents of the BPO. That is, the particles are not produced by dissolving in, and then crystallizing from, solvents and thus do not contain solvents. Instead a process is used that disperses BPO in water as a vehicle to prepare the BPO crystals.

In accordance with aspects of the invention, a composition containing BPO can be formulated into a finished dosage form and placed into contact with human skin or other tissue without causing significant irritation. The compositions containing this crystalline, fine, solvent-free, BPO can be dispersions or pastes depending on the concentration of BPO. Consequently, the compositions provide excellent vehicles for use in cosmetic lotions, gels, and creams, pharmaceutical preparations, and cleansing products.

In accordance with an aspect of the invention, solid BPO raw material is added to water and then milled to break up agglomerates. Sufficient water is added to form a flowable dispersion. For example, 35 to 55% benzoyl peroxide is added to 35 to 60% water. The milling process is temperature controlled using a chiller system so that the batch does not exceed 30° C. When an in-line mill is used for the milling process the amount of milling is determined by calculating the amount of time to make three complete theatrically passes through the mill for the entire batch. Milling is performed by a rotor mill such as a Ross Mill.

A dispersion system is then added to the batch and mixed in. The amount of the dispersion system depends on the actual ingredients used, but generally with by 0.2 to 4 wt % of the composition. The pH is adjusted to 2.8 to 6.6, typically 5.5 to 6.0, with a suitable amount of an alkaline agent such as, but not limited to, sodium hydroxide, potassium hydroxide or calcium hydroxide. The batch is then run through a second mill resulting in a fine particle size which is essentially free of particles greater than 25 microns. Milling is performed with a high pressure mill that forces the product through a small orifice causing particle collisions resulting in a size reduction (e.g., a Sonic Mill), for example, and then it is drummed off. The product is pumped from the manufacturing vessel into drums or pails. The drums and pails are then sold to customers. It is essentially the packaging step for the product. The resulting gel contains BPO in the form of small particles of BPO dispersed in water.

BPO in general is a soft plastic-like material that gets tacky when heated. It is preferable to avoid this tacky property. Therefore, the temperature of the mixture generally should not exceed 30° C. If necessary, various ingredients and/or batches should be cooled during the process.

The resultant BPO is devoid of particles greater than 25 microns, more particularly devoid of particles greater than 10 microns, and still more particularly devoid of particles greater than 5 microns, and still more particularly devoid of particles greater than 3 microns. In one aspect, the BPO has a mean particle size of 1 to 2 microns and, more particularly about 1.2 to 1.5 microns. The median particle size may be about 0.06 to 0.70 microns, for example, 0.65 microns. In another aspect, 5% of the particles are 0.35 microns or less, and 95% of the particles are 3.5 microns or less. The maximum particle size is 25 microns, more particularly 20 microns, still more particularly 10 microns, still more particularly 5 microns, and even more particularly 3 microns. The particles should be larger than nano-sized (greater than 0.10 microns) to reduce transdermal delivery.

The dispersant system typically contains suspending agent(s) gelling aid(s), buffering agent(s), defoamer(s), and/or dispersant(s) which are selected to be nonreactive with respect to benzoyl peroxide and nontoxic and therefore safe for topical application. The dispersant system does not contain a solvent.

Suitable suspending agents may include, but are not limited to, acrylates copolymer, acrylates/methoxy peg-15 methacrylate copolymer, acrylates/steareth-20 methacrylate crosspolymer, acrylates/vinyl isodecanoate crosspolymer, acrylates/vp copolymer, acrylic acid/acrylamidomethyl propane sulfonic acid copolymer, acrylic acid/vp crosspolymer, ammonium styrene/acrylates copolymer, ammonium va/acrylates copolymer, bentonite, biotite, butyl babassuate, calcium lignosulfonate, c4-24 alkyl dimethicone/divinyldimethicone crosspolymer, chitosan lauramide succinamide, cobalt dna, coralline officinalis powder, corn starch/acrylamide/sodium acrylate copolymer, dehydroxanthan gum, diallyloxyneohexyl zirconium tridecanoate, dehydrogenated tallow benzylmonium hectorite, dimethicone crosspolymer, dimethiconol/Stearyl methicone/phenyl trimethicone copolymer, dimethylol urea/phenol/sodium phenolsulfonate copolymer, dipentaerythityl pentaisostearate, disodium methylene dinaphthalenesulfonate, disteardimonium hectorite, ditrimethylolpropane isostearate/sebacate, ditrimethylolpropane triethylhexanoate, erythityl triethylhexanoate, ethylene/ma copolymer, ethylene/va copolymer, ethylhexyl hydroxystearoyl hydroxystearate, ethyl trisiloxane, feruloyl soy glycerides, glass, glass beads, hectorite, hydrogenated isocetyl olivate, hydrogenated lecithin, hydroxyethyl acrylate/sodium actyloyldimethyl taurate copolymer, hydroxyethyl pei-1000, hydroxyethyl pei-1500, hydroxypropyl starch, hydroxypropyltrimonium maltodextrin crosspolymer, isobutylene/ma copolymer, isopropyl babassuate, isopropyl ester of pvm/ma copolymer, magnesium phosphate, maltodextrin, methacrylol ethyl betaine/acrylates copolymer, methoxy peg-17/dodecyl glycol copolymer, methoxy peg-22/dodecyl glycol copolymer, methoxy peg-114/polyepsilon caprolactone, methyl methacrylate, myristoyl/pca chitin, nitrocellulose, octyldodecyl/ppg-3 myristyl ether dimmer dilinoleate, peg-18 castor oil dioleate, peg-150/decyl alcohol/smdi copolymer, peg-12 dimethicone crosspolymer, peg-150 stearyl alcohol/smdi copolymer, pei-7, pei-10, pei-15, pei-30, pei-35, pei-45, pei-250, pei-275, pei-700, pei-1000, pei-1400, pei-1500, pei-1750, pei-2500, pei-14m, pentafluoropropane, perfluoronyl octyldodecyl glycol meadowfoamate, perlite, phosphonobutanetricacarboxylic acid, polyacrylamidomethylpropane sulfonic acid, polyacrylate-10, polyacrylate-11, polycaprolactone, polyethylacrylate, polyglyceryl-4 isostearate/laurate, polyhydroxystearic acid, polyxymethylene cyanoguanidine urea, polyperfluorethoxymethoxy peg-2 phosphate, polyvinyl imidazolinium acetate, polyvinyl methyl ether, ppg-3 myristyl ether neoheptanoate, propylene glycol ricinoleate, pvm/ma copolymer, pvp, pvp/va/ltaconic acid copolymer, quaternium-18 bentonite, quatemium-18/benzalkonium bentonite, quaternium-18 hectorite, quaternium-90 bentonite, rhizobian gum, silica, silica dimethicone silylate, silica dimethyl silylate, silica silylate, sodium acrylate/sodium acryloyldimethyl taurate/acrylamide copolymer, sodium acrylates/vinyl isodecanoate crosspolymer, sodium acrylates/vinyl isodecanoate crosspolymer, sodium acrylic acid/ma copolymer, sodium acryloyldimethyl taurate/acrylamide/vp copolymer, sodium c4-12 olefin/maleic acid copolymer, sodium dextran sulfate, sodium dimaltodextrin phosphate, sodium glycereth-1 polyphosphate, sodium isooctylene/ma copolymer, sodium magnesium fluorosilicate, starch hydroxypropyltrimonium chloride, stearalkonium bentonite, stearalkonium hectorite, Stearyl/ppg-3 myristyl ether dimmer dilinoleate, stearylvinyl ether/ma copolymer, styrene/acrylates/acrylonitrile copolymer, styrene/acrylates/ammonium methacrylate copolymer, styrene/ma copolymer, sucrose benzoate/sucrose acetate isobutyrate/butyl benzyl phthalate copolymer, synthetic ruby, synthetic ruby powder, tosylamide/epoxy resin, tosylamide/formaldehyde resin, tribenzoyl triricinolein, vp/dimethylaminoethylmethacrylate copolymer, vp/eicosene copolymer, vp/hexadecene copolymer, vp/va copolymer.

Suitable gelling agents may include, but are not limited to, alcohol, alcohol denat., benzyl alcohol, 1,2-butanediol, butoxydiglycol, butoxyethanol, butylene glycol, cd alcohol 19, ceteareth-22, c7-8 isoparaffin, c8-9 isoparaffin, c9-11 isoparaffin, c9-13 isoparaffin, c9-14 isoparaffin, c10-11 isoparaffin, c10-12 isoparaffin, c11-14 isoparaffin, decane, decene, deodorized kerosene, diethylene glycol, dimethyl ether, dimethyl isosorbide, dimethyl sulfone, dipropylene glycol, dodecene, ethoxydiglycol, ethoxyethanol, ethyl perfluorobutyl ether, ethyl perfluoroisobutyl ether, ethyl trisiloxane, glycereth-7, glycereth-8, glycereth-12, glycereth-20, glycereth-26, glycereth-31, glycerin, glycofurol, glycol, heptane, hexadecene, hexane, 1,2,6-hexanetriol, hexyl alcohol, hexylene glycol, isobutoxypropanol, isopentane, isopropyl alcohol, methoxydiglycol, methoxyethanol, methoxyethanol acetate, methoxyisopropanol, methyl hexyl ether, methyl perfluorobutyl ether, methyl perfluoroisobutyl ether, octadecene, octane, pentane, polyglyceryl sorbitol, propanediol, propyl alcohol, propylene carbonate, propylene glycol, sd alcohol 1, sd alcohol 3-a, sd alcohol 3-b, sd alcohol 3-c, sd alcohol 23-a, sd alcohol 23-f, sd alcohol 23-h, sd alcohol 27-b, sd alcohol 30, sd alcohol 31-a, sd alcohol 36, sd alcohol 37, sd alcohol 38-b, sd alcohol 38-c, sd alcohol 38-d, sd alcohol 38-f, sd alcohol 39, sd alcohol 39-a, sd alcohol 39-b, sd alcohol 39-c, sd alcohol 39-d, sd alcohol 40, sd alcohol 40-1, sd alcohol 40-b, sd alcohol 40-c, sd alcohol 46, sorbeth-6, sorbeth-30, sorbeth-40, tetradecene, triethylene glycol, turpentine.

Suitable defoamers may include, but are not limited to, alcohol, alcohol denat., behenyl methacrylate/ethylamine oxide, methacrylate copolymet, bisphenylhexamethicone, cetyl dimethicone, c12-14 sec-pareth-5, dimethicone, dimethicone silylate, dimethiconol, diphenyl dimethicone, diphenylsiloxy phenyl trimethicone, disiloxane, fluoro c2-8 alkyldimethicone, hexadecyl methicone, hexyl alcohol, isopropyl alcohol, laureth-5 butyl ether, peg/ppg-8/26 dimethicone, peg/ppg-12/16 dimethicone, peg/ppg-12/18 dimethicone, peg/ppg-16/8 dimethicone, petroleum distillates, phenethyl disiloxane, phenyl dimethicone, phenyl trimethicone, polysilicone-1, polysilicone-2, polysilicone-7, polysilicone-8, polysilicone-10, propyl alcohol, silica dimethicone silylate, silica silylate, dimethicone, trimethylsiloxysilicate, trimethylsiloxysilicate/dimethicone crosspolymer, triphenyl trimethicone, trisiloxane.

Suitable buffering agents may include, but are not limited to, aluminum glycinate, aluminum lactate, ammonium acetate, ammonium carbonate, ammonium hexafluorophosphate, ammonium lactate, ammonium molybdate, ammonium phosphate, ammonium vanadate, boric acid, calcium carbonate, calcium phosphate, clay minerals, cyclohexylamine, decapeptide-7, diammonium citrate, diammonium phosphate, diethanolamine bisulfate, diethylamine, diethyl ethanolamine, disodium fumarate, disodium phosphate, disodium pyrophosphate, ectoin, ethanolamine hcl, glycine, hydroxyethylpiperazine ethane sulfonic acid, lauryl p-cresol ketoxime, lithium fluoride, magnesium acetate, magnesium lactate, mes-borate, methoxy peg-114/polyepsilon caprolactone, mipa-borate, phosphonobutanetricarboxylic acid, potassium acetate, potassium bicarbonate, potassium biphthalate, potassium citrate, potassium lactate, sodium acetate, sodium aluminate, sodium aluminum lactate, sodium bicarbonate, sodium citrate, sodium fumarate, sodium humate, sodium lactate, sodium phosphate, sodium silicate, sodium succinate, sodium trimetaphosphate, tetrapotassium pyrophosphate, tetrasodium pyrophosphate, trisodium sulfosuccinate, urea, zinc glycinate, zinc hexametaphosphate.

Suitable dispersants may include cellulosic derivatives and surfactants, including both anionic surfactants and nonionic surfactants, inorganic colloidal materials, and carboxyvinyl polymers (Carbomer). The dispersant may comprise cellulose ethers and cellulose esters such as carboxymethyl cellulose, hydroxyethyl cellulose, or hydroxypropylmethylcellulose; polysaccharide gums such as xanthan gums, guar gums, carrageenan gum, modified starches such as the modified potato starch and the like, polyacrylamides such as polyacrylamide/C13-14 isoparaffin/laureth-7 mixture, a mixture of sodium acryloyldimethyltaurate copolymer/isohexadecane/polysorbate 80; acrylic polymers coupled to hydrophobic chains, such as the PEG-150/decyl/SMDI copolymer, aluminum/magnesium silicate, polyvinyl alcohol, polyethylene oxides, propylene glycol alginates or mixtures thereof. Particular dispersants include 1,3 Propanediol and sodium dioctyl sulfosuccinate.

The final pH of the gel or dispersant containing BPO is 2.8 to 6.6, typically 5.5 to 6.

The BPO compositions disclosed herein provide several advantages over prior compositions that are not made with the disclosed BPO particle size in accordance with the disclosed process conditions. The instant compositions are less irritating or non-irritating and less sensitizing or non-sensitizing than compositions made using larger particle size BPO or compositions containing BPO solvents. The compositions are also more effective and/or can be applied in amounts that are more effective in relation to killing *p. acnes* and related bacteria. They can also be formulated to exhibit less tendency to cause de-pigmentation (bleaching effect) of the skin.

The BPO can be added to other ingredients or vehicles often used in cosmetic products, e.g., emulsions, lotions, creams or gels at low temperatures to provide finished products.

In one aspect, a gel former pre-mix is prepared by adding an appropriate quantity of water to a side mixing tank, adding the gel former, and then allowing the gel-former to completely wet-out. After wet-out, the gel former is mixed until the gel former is completely hydrated. Mixing is continued until the gel-former is added to the main batch.

A main batch is formed by, for example, adding water, sodium citrate, defoamer, dactyl sodium sulfosuccinate, and propanediol to a main mixing tank and mixing until uniform. The main batch may be re-circulated with a Ross mill. Raw BPO is added to the main batch with re-circulation and milling. After all of the BPO is added, the Ross mill is shut off and the gel former pre-mix is added to the main batch and mixed until the gel former is uniformly distributed through the batch. Sodium hydroxide is added to the main batch at a sufficient quantity to neutralize the dispersant and obtain the desired pH. The main batch is run through a homogenizer and filled into containers.

In these processes, the BPO is never in contact with substantial heat; thus the possibility of decomposition or fire is greatly reduced. The BPO compositions disclosed herein are also more stable and safer for transportation as determined by Department of Transportation (DOT) standards. That is, in the disclosed gel form, the likelihood of enough BPO accumulating to become explosive or a fire hazard is reduced. While DOT regulations limit the maximum BPO concentration to 40% by weight, the compositions disclosed herein can be used in higher concentrations because they have less tendency to agglomerate and therefore maintain their stability. Additionally, while certain known BPO gel compositions tend to harden or thicken upon storage, especially at lower temperatures, the compositions disclosed herein do not tend to harden and/or thicken to a lesser degree than known compositions. Testing included attempts to ignite the material, exposing the product to elevated temperatures (70° C. for 72 hours), and impact and friction testing. In all cases the 40% material was unreactive and stable.

Example 1

The following BPO composition was prepared by combining water, BPO, other ingredients, milling, and then adding a neutralizing agent.

| Component | Purpose | Percent range |
| --- | --- | --- |
| Water | Vehicle | 42-46% |
| Raw benzoyl peroxide | Active | 52-54% |
| Sodium Citrate | Buffer | 0.9-1.1% |
| Starsil AF30FC | Defoamer | 0.09-0.11% |
| Gemtex SC-70-P | Dispersing Aids | 1.3-0.71% |
| Zemea | | |
| Carpobol Ultrex 10 | Suspending Aid | 0.35-0.45% |
| Sodium hydroxide | Neutralizing agent | To spec |

Starsil AF30FC, Starchem, LLC: dimethicone, silica, sorbitan stearate, sorbitan stearate, PEG-40, xanthan gum.
Gemtex SC-70-P, Innospec Active Chemicals, LLC: sodium dioctyl sulfosuccinate.
Zemea, DuPont, Tate & Lyle Bioproducts: 1,3 Propanediol
Carpobol Ultrex 10, Lubrizol: Carbomer Accelerated stability studies at 40° C. and 75% relative humidity to determine whether there is degradation of the BPO over time.

| | |
| --- | --- |
| Initial | 43.04% BPO |
| 2 months | 40.07% BPO |
| 3 months | 40.76% BPO |
| 4 months | 40.69% BPO |
| 6 months | 40.72% BPO |

Example 2

Twenty-five subjects ages 20-65 were requested to bathe or wash as usual before arrival at the facility. Qualified subjects were then prepared for patch application by having the test sites wiped with alcohol and air-dried. Patches dosed with 0.2 ml or 0.2 g of a 10% active BPO dispersion (prepared from a 40% dispersion as the source for the BPO), patches dosed with positive (1.0% Sodium Lauryl Sulfate (SLS) solution), and patches dosed with negative (undosed semi-occlusive patch) controls were then applied directly to the skin of the infrascapular regions of the back, to the right or left of the midline on every day of the week for the first 12 days and the subject was dismissed with instructions not to wet or expose the test area to direct sunlight. Patches were applied for approximately a 24 hour period, then removed and discarded by the subject approximately two hours prior to grading. All induction patches were applied to the same sites unless the degree of reaction (cumulative grade 3) to a material or the adhesive necessitated removal. The skin adjacent to the patches was marked using a surgical marker or other suitable marking pen. Prior to each reapplication, the test sites were evaluated. At the final visit, no patches were applied and the patch sites were graded. Skin responses were evaluated according to the following scale by a technical associate of AMA Laboratories, Inc. (scorer) trained in the evaluation of skin using consistent adequate lighting from a 60-watt incandescent blue day light bulb to illuminate the patch area. All reasonable attempts were made to ensure that the same individual did all of the scoring of reactions to the test articles during the course of the study, and was blinded to the treatment assignments and any previous scores.

Scoring of Test Sites:
Skin reactions at the patch sites were assigned using the following scale:
0 No evidence of irritation
1 Minimal erythema, barely perceptible
2 Definite erythema, readily visible; or minimal edema; or minimal papular response
3 Erythema and papules
4 Definite edema
5 Erythema, edema, and papules
6 Vesicular eruption
7 Strong reaction spreading beyond test site Effects on superficial layers of the skin were scored as follows:
A Slight glazed appearance
B Marked glazing
C Glazing with peeling and cracking
D Glazing with fissures
E Film of dried serous exudate covering all or portion of the patch site
F Small petechial erosions and/or scab For cumulative scoring purposes, any score of 3 or higher was considered to be a 3 for the remainder of the test, even though applications for that test site were discontinued. The actual patch test scores were the combination of a numerical and/or letter score consistent with the definitions given in the scoring scale. Scores containing letter grades were converted into numerical equivalents as follows: A=0, B=1, C=2, and D, E, and F=3. These equivalents were considered additive to any numerical score (e.g., 2C=2+2=4).

All scorers were required to take and pass a visual discrimination examination conducted by a board certified ophthalmologist using the Farnsworth-Munsell 100 Hue test. This test, which determines a person's ability to discern color against a black background, was modified to incorporate a flash tone background (instead of black) to simulate the actual use conditions.

The test material was applied five days weekly for 12 days to the same site, or until irritation scores of 3 were observed. In this case application of the test sample is discontinued and the score attained is entered for the balance of the 12 day test. New test patches were applied to the test sites after visual evaluation.

Statistics and Data Management:

To obtain classifications of the test materials, subject scores were totaled for each test site. A standardized interpretation system for base (n=10) irritation scores during induction at 14 days was established by Berger and Bowman (Berger R. S. and J. P. Bowman, A reappraisal of the 21-day cumulative irritation test in man, J. Toxicol.—Cut. & Ocular Toxicol. 1 (2), 109-115, 1982). This system has been adjusted proportionally for 12 days of induction and for base (n=25). Categories were based on percentages of the maximum possible score for each test site. For the calculation of a total score, an upper limit of 3 was used. For cumulative scoring purposes, any score of 3 or higher was considered to be a 3 for the remainder of the test, even though applications for that test site are discontinued.

The following classification system was used evaluation of the results:

| Score | Indications from Test | Description of Observed Response |
|---|---|---|
| 0 to 70.71 | Mild material—no experimental irritation | Essentially no evidence of cumulative irritation under the conditions of test (i.e., continuous at concentration specified) |
| >70.71 to 285 | Probably mild in normal use | Evidence of slight potential for very mild cumulative irritation under conditions of test |
| >285 to 640.71 | Possibly mild in normal use | Evidence of moderate potential for mild cumulative irritation under conditions of test |
| 640.71 to 829.29 | Experimental cumulative irritant | Evidence of strong potential for mild-to-moderate cumulative irritation under conditions of test |
| >829.29 to 900 | Experimental Primary irritant | Evidence of potential for primary irritation under conditions of test |

Mean cumulative irritation scores were compared among the sites using two tailed Student's T-test with paired comparisons. All differences were considered significant at the $p<0.05$ level. The maximum potential score for a test material was calculated by multiplying the maximum potential daily score (3) by the number of panelists completing the study by the number of days of evaluation (9). In the event of an adverse reaction, the area of erythema and edema was measured. The edema was estimated by the evaluation of the skin with respect to the contour of the unaffected normal skin. Accompanying edema (swelling), if any, at any test site was recorded with an "e" and is described as mild, moderate or severe as compared with the normal surface of surrounding skin. Clients were notified immediately in the case of an adverse reaction and determination was made as to treatment program if necessary.

The results of panelists treated with the test material exhibited total cumulative irritancy score of 6. When compared to the negative control site—blank undosed semi-occlusive patch, which showed cumulative irritancy score of 0 and the positive control, semi-occlusive patch dosed with one hundred (100) microliters of a 1.0% Sodium Lauryl Sulfate (SLS), which showed cumulative irritancy score of 78. The test material presented essentially no evidence of cumulative irritation under the conditions of test.

The BPO used herein is advantageous because, unlike the crystals obtained by precipitation described in U.S. Pat. No. 4,401,835, the BPO particles are obtained by finely milling the compound. Precipitation is disadvantageous because it introduces solvents for the BPO that are difficult to remove completely and that can sensitize and irritate the skin especially in the presence of the fine particle size BPO. Accordingly, whereas in accordance with U.S. Pat. No. 4,401,835, small particle size BPO is obtained by precipitation and introducing BPO solvents that may enhance skin sensitivity and skin irritation, in accordance with the invention, the BPO is obtained by milling in the absence of BPO solvents to provide a product that is free of both irritating large particles and solvent. The fine particle size of the instant product and the absence of solvents is believed to make the material especially desirable for use in cosmetic products.

An additional characteristic of suspensions of BPO is the tendency for the BPO particles to re-agglomerate. In using the dispersion system disclosed herein, there is a reduced level of re-agglomeration which manifests itself in the improved safety profile in regard to the results of the DOT testing. This effect will potentially allow for a more efficient final product for topical use.

The low sensitivity and irritation experienced with the BPO of the invention, makes it useful in certain applications where patients with sensitive skin were not able to use other forms of BPO. Because the BPO used herein is not an irritant or sensitizer, it can be used in cases where patients show irritation to other forms of BPO. It is further believed that the BPO disclosed herein can be used in cases of clinically diagnosed sensitive skin. Similarly, patients exhibiting a high sensitivity to BPO who might not have been treatable with more irritating BPO compositions may be treated using the BPO described herein.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. A method of preparing crystalline, solvent-free, benzoyl peroxide particles comprising:
adding water to solid benzoyl peroxide;
milling to break up agglomerates and form an aqueous benzoyl peroxide composition;
adding a dispersion system and mixing;
adjusting the pH to 2.8 to 6.6; and
milling to a particle size not more than 25 microns.

2. The method of claim 1 wherein the pH is adjusted to 5.5 to 6.

3. The method of claim 1 wherein the pH is adjusted by adding an effective amount of sodium hydroxide potassium hydroxide or calcium hydroxide.

4. The method of claim 1 wherein the milling is performed with a rotor mill.

5. The method of claim 1 wherein the temperature is maintained below 30° C.

6. The method of claim 1 wherein the particle size is not greater than 10 microns.

7. The method of claim 1 wherein at least 90% of the particles are less than 3.5 microns in size.

8. The method of claim 1 wherein at least 95% of the particles are less than 3.5 microns in size.

9. The method of claim 1 wherein an average particle size is from 1 to 2 microns.

10. The method of claim 1 wherein the dispersion system comprises at least one selected from the group consisting of suspending agents, gelling aids, buffering agents, and dispersants.

11. The method of claim 1 wherein the water is added to solid benzoyl peroxide in the absence of solvents.

12. A method of making a therapeutic or cosmetic composition comprising preparing crystalline, solvent-free, benzoyl peroxide particles in accordance with claim 1; then adding the benzoyl peroxide particles to a water-based gel.

13. The method of claim 12 wherein the particle size is not greater than 10 microns.

14. The method of claim 12 wherein at least 90% of the particles are less than 3.5 microns in size.

15. The method of claim 12 wherein at least 95% of the particles are less than 3.5 microns in size.

16. The method of claim 12 wherein an average particle size is from 1 to 2 microns.

17. The method of claim 12 wherein the water-based gel comprises a dispersing system.

18. The method of claim 17 wherein the dispersion system comprises at least one selected from the group consisting of suspending agents, gelling aids, buffering agents, and dispersants.

19. The method of claim 17 wherein the composition contains about 25 to 65% by weight benzoyl peroxide.

* * * * *